(12) United States Patent
Silverman et al.

(10) Patent No.: US 6,794,413 B1
(45) Date of Patent: Sep. 21, 2004

(54) COMPOUNDS AND RELATED METHODS FOR INHIBITION OF γ-AMINOBUTYRIC ACID AMINOTRANSFERASE

(75) Inventors: Richard B. Silverman, Northbrook, IL (US); Yue Pan, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/623,152

(22) Filed: Jul. 18, 2003

Related U.S. Application Data
(60) Provisional application No. 60/397,498, filed on Jul. 19, 2002.

(51) Int. Cl.[7] .......................... A61K 31/557; C07C 61/20
(52) U.S. Cl. ........................................ 514/573; 562/504
(58) Field of Search ........................... 562/504; 514/573

(56) References Cited

PUBLICATIONS

Lippert B.; Metcalf, B. W.; Jung, M. J.; Casara, P: 4–Amino–hex–5–enoic acid, a selective catalytic inhibitor of 4–aminobutyric–acid aminotransferase in mammalian brain. Eur. J. Biochem. 1977, 74, 441–445.

Dewey, S. L.; Morgan, A. E.; Ashby, C. R., Jr.; Horan, B.; Kushner, S. A.; Logan, J.; Volkow, N. D.; Fowler, J. S.; Gardner, E. L.; Brodie, J. D. A novel strategy for the treatment of cocaine addiction. Synapse 1998, 30, 119–129.
Dewey, S. L.; Brodie, J. D.; Gerasimov, M.; Horan, B.; Gardner, E. L.; Ashby, C. R., Jr. A pharmacologic strategy for the treatment of nicotine addiction. Synapse 1999, 31, 76–86.
Gerasimov, M. R.; Ashby, C. R.; Gardner, E. L.; Mills, M. J.; Brodie, J.D.; Dewey, S. L. Gamma–vinyl GABA inhibits methamphetamiine, heroin, or ethanol–induced increases in nucleus accumbens dopamine. Synapse 1999, 34, 11–19.
Pan, Y.; Qiu, J.; Silverman, R. B. Design, synthesis, and biological activity of a difluoro–substituted, conformationally rigid vigabatrin analogue as a potent γ–aminobutyric acid aminotransferase inhibitor. J. Med. Chem. 2003, 46, 5292–5293.

Primary Examiner—Johann Richter
Assistant Examiner—Paul A. Zucker
(74) Attorney, Agent, or Firm—Reinhart Boerner Van Deuren s.c.

(57) ABSTRACT

(1S, 3S)-3-Amino-4-difluoromethylene-1-cyclopentanoic acid illustrates a novel class of compounds as potent irreversible inhibitors of γ-aminobutyric acid aminotransferase (GABA-AT). The corresponding monofluoro-substituted compounds also are potent time-dependent inhibitors of GABA-AT.

35 Claims, 1 Drawing Sheet

COMPOUNDS AND RELATED METHODS FOR INHIBITION OF γ-AMINOBUTYRIC ACID AMINOTRANSFERASE

This application-claims priority benefit from provisional application Ser. No. 60/397,498 filed Jul. 19, 2002, the entirety of which is incorporated herein by reference.

The United States government has certain rights to this invention pursuant to Grant No. NS15703 from the National Institutes of Health to Northwestern University.

BACKGROUND OF THE INVENTION

Epilepsy is an important central nervous system disease characterized by recurring convulsive seizures. It has been shown that convulsions arise when an imbalance exists between two principal neurotransmitters, L-glutamic acid, an excitatory neurotransmitter, and γ-aminobutyric acid (GABA), an inhibitory neurotransmitter. Two enzymes, glutamic acid decarboxylase (GAD) and γ-aminobutyric acid aminotransferase (GABA-AT), regulate the level of GABA in the brain. GAD synthesizes GABA from L-glutaric acid. GABA-AT, which is a pyridoxal-5'-phosphate (PLP, 1) dependent enzyme, converts GABA to succinic semialdehyde. During transamination, PLP is converted to pyridoxamine-5'-phosphate (PMP), which is transformed back to PLP by a reaction with 2-ketoglutarate; the 2-ketoglutarate is converted to L-glutamnic acid. Succinic semialdehyde dehydrogenase (SSDH) oxidizes succinic semialdehyde to succinic acid using $NADP^+$ as the cofactor (Scheme 1).

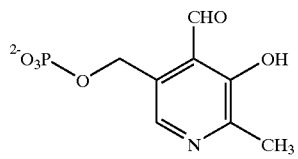

Scheme 1

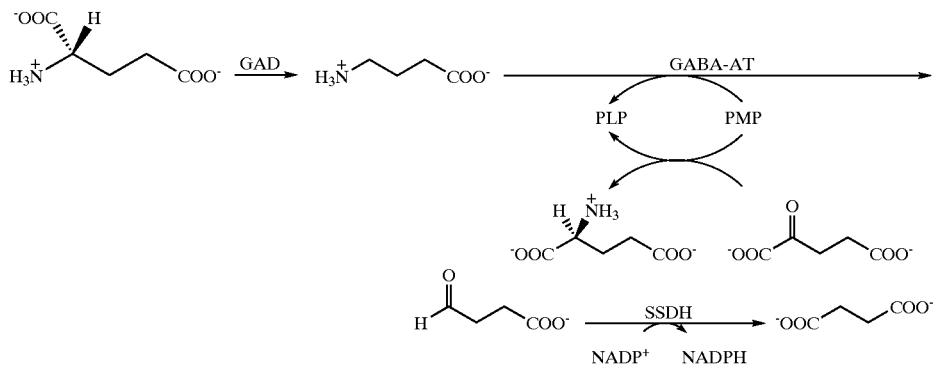

When the level of GABA in the brain falls below a threshold level, convulsions occur. Taking GABA orally is not effective in raising the GABA level in the brain because GABA cannot cross the blood-brain barrier. One promising approach is to inhibit GABA-AT, which degrades GABA. The level of GABA would increase due to its continuous production. The catalytic mechanism of GABA-AT is shown in Scheme 2. The cofactor PLP is bound to Lys329 in the form of a Schiff base. (Storici, P., Capitani, G.; Biase, D. D.; Moser, M.; John, R. A.; Jansonium, J. N.; Schirmer, T. Crystal Structure of GABA-Aminotransferase, a Target for Antiepileptic Drug Therapy. *Biochemistry*, 1999, 38, 8628–8634.) Transimination gives the imine between GABA and PLP. The enzyme then removes the γ-proton of GABA to give the aldimine, which is subsequently hydrolyzed to produce succinic semialdehyde and PMP.

In the art, it is understood by definition that a mechanism-based irreversible inhibitor is an unreactive compound that has a structural similarity to the substrate or product for the target enzyme and is converted by the target enzyme into a species that inactivates the enzyme prior to its release from the active site. (Silverman, R. B. *Mechanism-Based Enzyme Inactivation: Chemistry and Enzymology*, Vol. I; CRC Press: Boca Raton, 1988.) One such inhibitor is the rationally designed vigabatrin (2), an epilepsy drug marketed all over the world, except in the U.S., which irreversibly inhibits GABA-AT by the mechanisms shown in Scheme 3. Pathway a (Michael addition) has been determined and found to account for about 70–75% of the total inactivation. (Nanavati, S. M.; Silverman, R. B. Mechanisms of Inactivation of γ-aminobutyric Acid Aminotransferase by the Antiepilepsy Drug γ-Vinyl GABA (Vigabatrin). *J. Am. Chem. Soc.* 1991, 113, 9341–9349.)

Scheme 2ᵃ

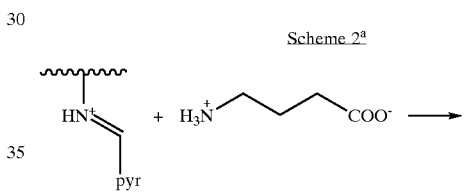

-continued

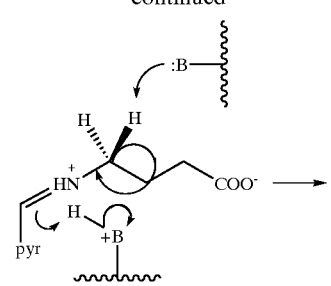

-continued

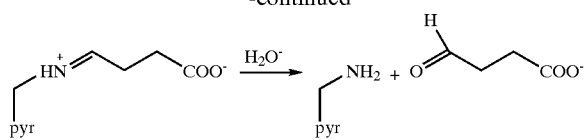

a. The Symbol Pyr Stands for the Pyridine Ring of PLP

Scheme 3

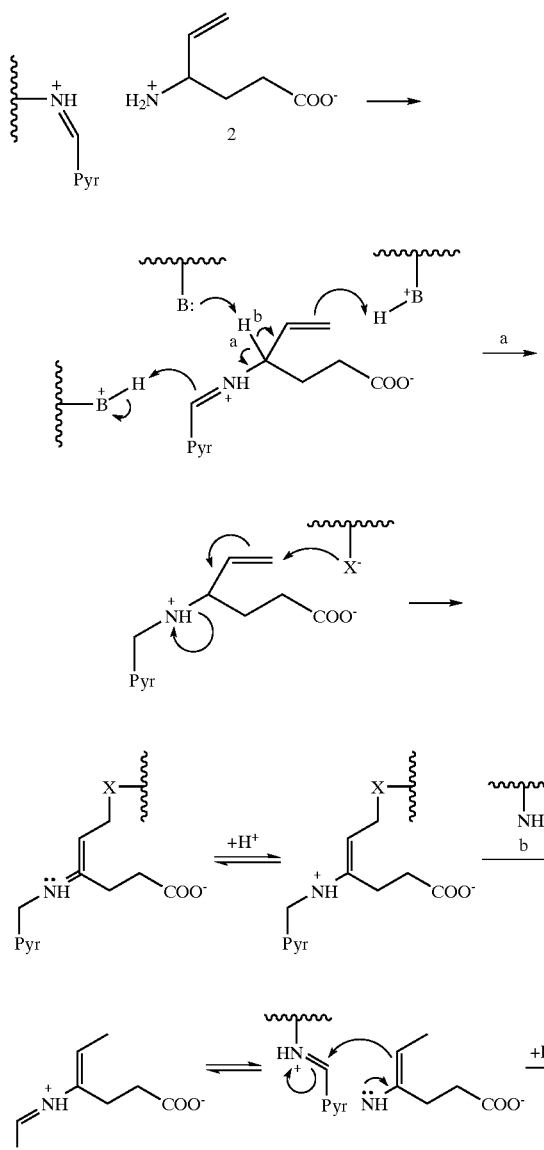

Previously, 3, a conformationally-rigid vigabatrin analogue, was synthesized.

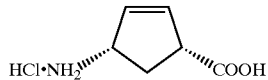

3

Surprisingly, 3 was not a GABA-AT inactivator but was a very good substrate ($K_m$=0.1 mM, $k_{cat}$=11.7 min$^{-1}$, $k_{cat}/K_m$= 117 mM$^{-1}$ min$^{-1}$) with a specificity constant almost six times greater than that of GABA ($K_m$=2.4 mM, $k_{cat}$=49 min$^{-1}$, $k_{cat}/K_m$=20.4 mM$^{-1}$ min$^{-1}$). It was later determined by computer modeling that the endocyclic double bond is not in the right orientation for Michael addition (pathway a, Scheme 3), nor is it an effective enamine for enzyme inactivation. Therefore 7, which has an exocyclic double bond, was designed and prepared from diketone 4, as shown in Scheme 4. (Qiu, J.; Pingsterhaus, J. M.; Silverman, R. B. Inhibition and Substrate Activity of Conformationally Rigid Vigabatrin Analogues with γ-Aminobutyric Acid Aminotransferase. *J. Med. Chem.* 1999, 42, 4725–4728.) An addition reaction with (trimethylsilyl)methylmagnesium chloride followed by elimination furnished 6. Deprotection of the benzyl group and hydrolysis of the lactam gave the amino acid 7. (Specific reagents and conditions: (a) TMSCH$_2$MgCl, −30° C. to RT, 38%; (b) (CF$_3$CO)$_2$O, DMAP, then TBABr, KF, 86%; (c) Na/NH$_3$/$^t$BuOH,; (d) 2N HCl, 90%, 2 steps.)

Scheme 4

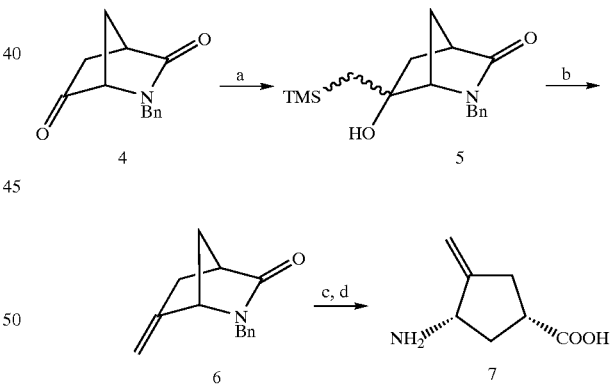

Interestingly, 7 inactivated GABA-AT, but when 2-mercaptoethanol was added to the incubation mixture, no inactivation was observed. A possible mechanism accounting for this phenomenon is shown in Scheme 5. It is likely that 7 is only a substrate for GABA-AT. After formation of 8, the double bond is not reactive enough, so this intermediate is not trapped by the enzyme, but rather is released from the active site in the form of an α,β-unsaturated ketone (9). In the presence of 2-mercaptoethanol, a reactive nucleophile, 9 is trapped to form 10, giving no inactivation

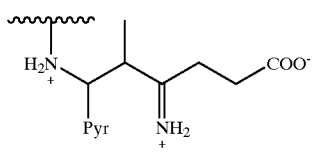

Scheme 5

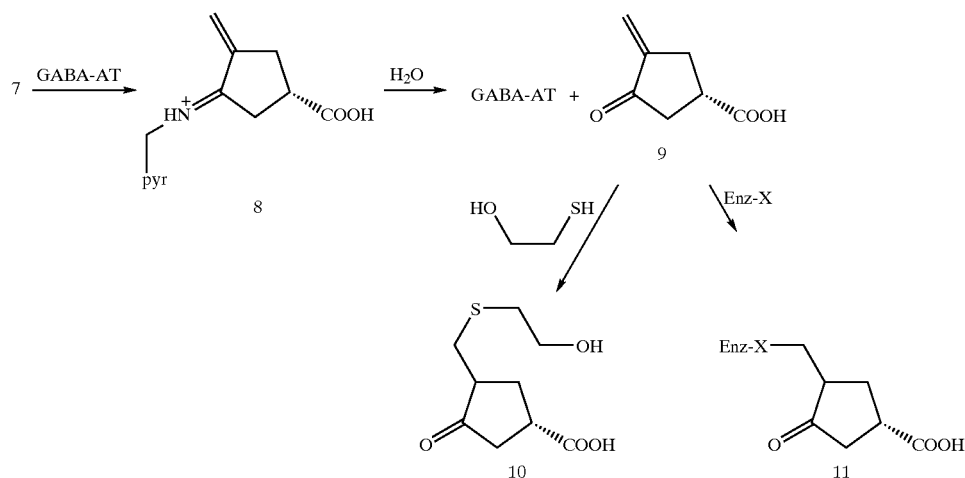

of the enzyme. In the absence of 2-mercaptoethanol, however, 9 may return to the enzyme and become covalently attached to the enzyme (11), leading to the enzyme's inactivation. According, however, to definitions, prior art compound 7 is not a mechanism-based inactivator inasmuch as inactivation does not occur prior to the release of the active species from the active site.

SUMMARY OF THE INVENTION

Figure 1:
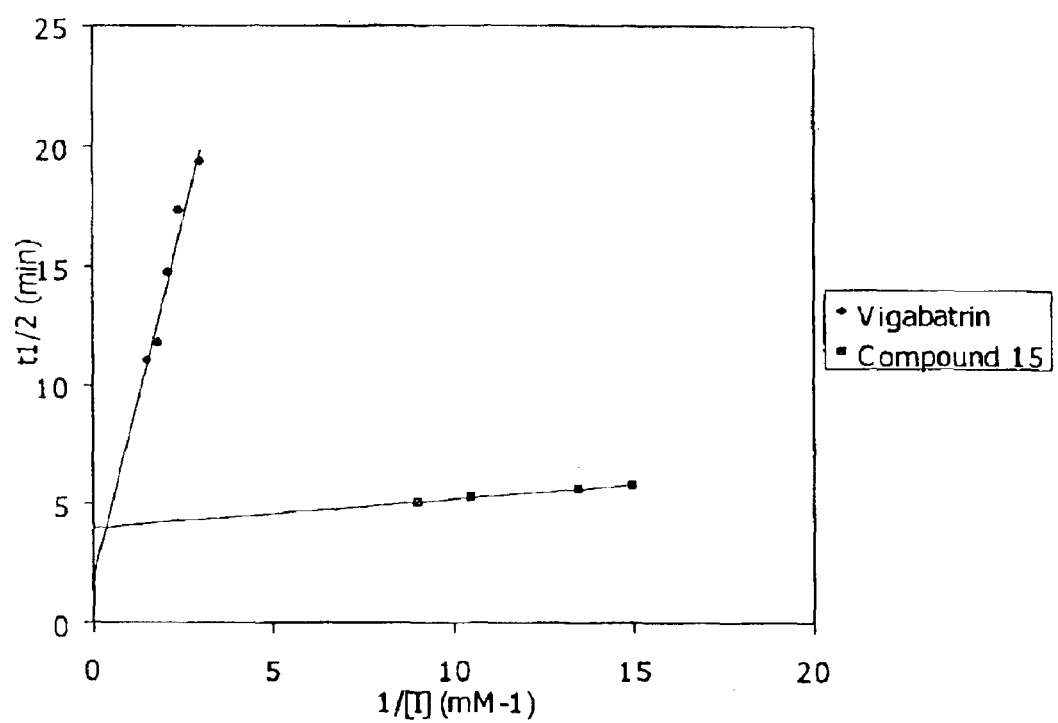
FIG. 1 graphically compares activities of vigabatrin (♦) and a difluoro-substituted compound (■), 15, in accordance with this invention. For vigabatrin: $y=6.0295x+1.8585$, and $R^2=0.9553$. For compound 15: $y=0.1227x+3.948$, and $R^2=0.9965$.

In light of the foregoing, it is an object of the present invention to provide various compounds and/or compositions and related methodologies for the inactivation and/or inhibition of γ-aminobutyric acid aminotransferase, such inactivation or inhibitory activity as can be used in the treatment of epilepsy and other CNS disease states, including addiction, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a mechanism-based inhibition and/or inactivation methodology and one or more compounds useful in conjunction therewith.

It is another object of the present invention to provide one or more compounds demonstrating inhibitory activity with respect to γ-aminobutyric acid aminotransferase, such activity as would be understood by those skilled in the art to be efficacious in the treatment of epilepsy and addiction.

It is another object of the present invention to provide one or more compounds incorporating rationally-designed structural characteristics consistent with mechanism-based inhibition/inactivation of γ-aminobutyric acid aminotransferase, such compounds having incorporated therein an electron-deficient methylene moiety for irreversible interactive contact with an active site of such an enzyme.

Other objects, features, benefits and advantages of the present invention will be apparent from this summary and its descriptions of certain embodiments, and will be readily apparent to those skilled in the art having knowledge of various enzyme systems, and inhibitory compounds and their preparation. Such objects, features, benefits and advantages will be apparent from the above as taken into conjunction with the accompanying examples, data, figures and all reasonable inferences to be drawn therefrom.

In part, the present invention comprises a γ-aminobutyric acid aminotransferase inhibitor compound of a formula

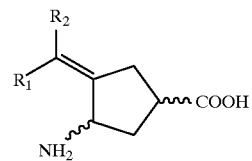

wherein $R_1$ and $R_2$ are selected from H and F, and at least one of $R_1$ and $R_2$ is F Alternatively, such inhibitors can be salts of such a compound; that is, including but not limited to an ammonium salt or a carboxylate salt of such a compound. Whether monofluoro- or difluoro-substituted, the amino and carboxy substituents can have either a cis or trans stereochemical relationship. In monofluoro-substituted embodiments, such compounds can have either a Z or an E configuration.

As shown below in the context of several synthetic preparations, certain embodiments of the present inhibitor compounds can be provided as an ammonium salt, wherein the counter ion is the conjugate base of a protic acid. Likewise, in various other embodiments, such inhibitor compounds can be provided and/or utilized as a carboxylate, in conjunction, for example, with a corresponding ammonium (e.g., $+NHR_3$, where R is hydrogen or alkyl), alkaline or alkaline-earth cation. Without limitation, certain preferred embodiments of this invention can comprise monofluoro- or difluoro-substituted compounds as either the ammonium hydrochloride salt or sodium carboxylate.

As discussed more fully below in conjunction with known and accepted mechanistic considerations, the present invention can also include a complex comprising the addition product of a γ-aminobutyric acid aminotransferase and a compound of this invention, such a complex inactivating the enzyme component thereof. Without limitation, such compounds include those discussed more fully above and illustrated below, all as can be varied in accordance within the range of stereochemical and/or configurational relationships contemplated within the broader aspects of this invention. As would be understood by those skilled in the art, the enzyme component of such an addition product further comprises a pyridoxal-5-phosphate cofactor.

Accordingly, the present invention also includes a method of inhibiting a γ-aminobutyric acid aminotransferase. Such a method comprises contacting the enzyme with at least a partially effective amount of one of the aforementioned inventive compounds. Such contact would be as understood by those skilled in the art experimentally and/or for research purposes or as may be designed to simulate one or more in vivo or physiological conditions. In certain embodiments, an addition can be achieved with one or more difluoro-substituted compounds. In other embodiments, monofluoro-substituted compounds can be used with comparable effect. Regardless of fluoro-substitution, the amino and carboxy substituents can vary by degree of protonation and the presence as the corresponding salt. Likewise, such compounds are considered over the full range of stereochemical and/or configurational isomers.

Moreover, in yet another departure from the prior art, the present invention provides a method of using an electron-deficient exocyclic methylene moiety to inhibit γ-aminobutyric acid aminotransferase activity. Such a method comprises (1) providing a compound from a group of compounds of a formula

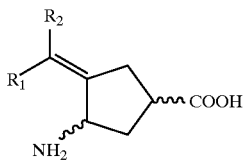

wherein $R_1$ and $R_2$ are selected from H and F, and at least one of $R_1$ and $R_2$ is F; such compounds including salts thereof; and (2) contacting such a compound with a γ-aminobutyric acid aminotransferase, the exocyclic methylene moiety of the compound capable of binding to an active site residue of the enzyme. Without limitation, such compounds are either monofluoro- or difluoro- substituted, and can vary within the fill range of structural, ionic, stereochemical and/or configurational considerations discussed above. Nonetheless, certain cis and trans isomers are used, as provided in the following examples, to demonstrate one or more aspects regarding the utility of this invention.

Because prior art methylene compound 7 did not inactivate GABA-AT, an approach was taken to design the compounds of this invention, in particular the more reactive, difluoro-substituted compound 15. Without limitation to any one theory or mode of operation, the comparable size but higher electronegativity of fluorine, as compared to hydrogen, provides a much more reactive intermediate. Prior to its release, this species may be sufficiently reactive to become covalently attached or bound to GABA-AT upon contact or reaction therewith, leading to enzyme inactivation. Illustrating such embodiments, compound 15 was prepared from 12 (Scheme 6). Compound 13 was prepared by a Horner-Wadsworth-Emmons reaction. (Piettre, S. R.; Cabanas, L. Reinvestigation of the Wadsworth-Emmons Reaction Involving Lithium Difluoromethylenephosphonate. *Tetrahedron Lett.* 1996, 37, 5881–5884.) It was then deprotected using ceric ammonium nitrate (CAN) to give 14 and hydrolyzed to give 15. (Qiu, J.; Silverman, R. B. A New Class of Conformationally Rigid Analogues of 4-Amino-5-halopentanoic Acids, Potent Inactivators of γ-Aminobutyric Acid Aminotransferase. *J Med. Chem.* 2000, 43, 706–720) (See, more particularly, examples 5–7, below.)

Scheme 6

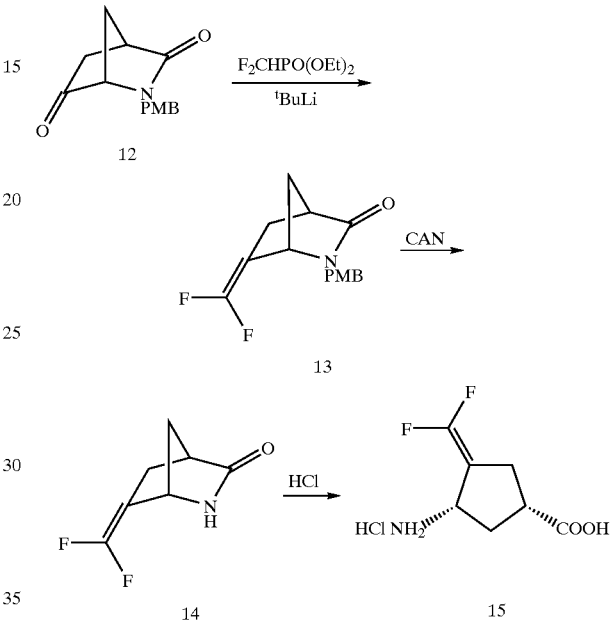

Compound 15 was found to be a very potent GABA-AT inactivator, even in the presence of 2 mM 2-mercaptoethanol. Because of its high potency, $k_{inact}$ and $K_I$ values could not be determined accurately under optimal conditions (pH 8.5, 25 °C.), where the enzyme exhibits maximum activity. Comparisons were made with (S)-vigabatrin of the prior art. Taking only the first two data points for both 15 and (S)-vigabatrin, the $k_{inact}/K_I$ value for 15 is 186 times greater than that for (S)-vigabatrin. In order to obtain more accurate data, 15 and vigabatrin were compared under nonoptimal conditions. Even at 0° C. in pH 8.5 buffer, no pseudo first-order kinetics were observed for 15. At pH 6.5 (25° C.) 15 ($K_I$ 31 μM, $k_{inact}$ 0.18 min$^{-1}$, $k_{inact}/K_I$ 5.7 mM$^{-1}$ min$^{-1}$) is 50 times more potent than (S)-vigabatrin ($K_I$ 3.24 mM, $k_{inact}$ 0.37 min$^{-1}$, $k_{inact}/K_I$ 0.114 mM$^{-1}$min$^{-1}$). (See also example 14 and FIG. 1.) The exocyclic methylene moiety and/or the rigid conformation of 15, which is believed to minimize the entropic penalty on binding, may contribute to its potency. Fluorine incorporation may also make a corresponding intermediate sufficiently reactive to be trapped by the enzyme. While the cis isomer is shown in Scheme 6. Comparable results can be obtained with the trans isomer, as can be prepared through a straight-forward extension of the synthetic techniques described herein, as would be understood by those skilled in the art.

Likewise, this invention contemplates various monofluoro-substituted compounds. The syntheses of compounds 20 and 22 are shown in Scheme 7. The reaction of prior art starting material 12 with fluoromethylphenylsulfone and diethylphosphoryl chloride gave 16 as a mixture of the two isomers, which was then subjected to the reduction with magnesium and mercury chloride, giving 17 and 18 which were separated and isolated. Further deprotection of the lactam then hydrolysis gave 20 and 22. (See examples 8 and 13, below.) Consistent herewith, compounds 20 and 22 also are potent time-dependent inhibitors of GABA-AT. Similar activities can be demonstrated with the corresponding trans isomers.

silica gel 60 F254 preloaded glass plates. Cation-exchange resin was purchased from Bio-Rad Laboratories. An Orion Research 702 pH meter with a general combination electrode was used for pH measurements. All enzyme assays were recorded on a Perkin-Elmer Lambda 10 UV/V is spectrometer.

Reagents. Fluoromethyl phenylsulfone was purchased from TCI America, Inc. All other reagents were purchased

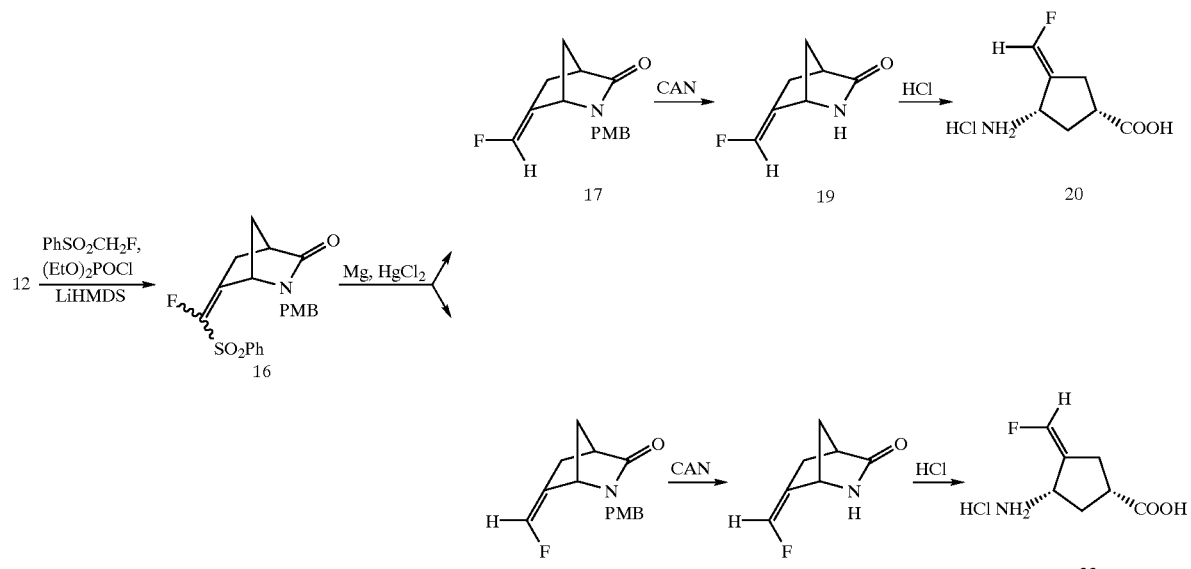

Scheme 7

EXAMPLES OF THE INVENTION

The following non-limiting examples and data illustrate various aspects and features relating to the compounds and/methods of the present invention, including the preparation of molecular compounds having various structural moieties for inhibitory interaction with a γ-aminobutyric acid aminotransferase, such compounds as are available through the synthetic methodologies described herein. In comparison with the prior art, the present methods and compounds provide results and data which are surprising, unexpected and contrary to the prior art. While the utility of this invention can be illustrated through the use of several compounds and structural moieties incorporated therein, it will be understood by those skilled in the art that comparable results are obtainable with various other compounds and moieties consistent herewith and as are commenced right with the sculpt of this invention.

General Methods. All NMR spectra were recorded on either a Varian Mercury 400 MHz or a Varian Inova 500 MHz NMR spectrometer. $^1$H chemical shifts are reported as δ values in ppm downfield from Me$_4$Si as the internal standard in CDCl$_3$. For samples run in D$_2$O, the HOD resonance was set at 4.80 ppm. $^{13}$C chemical shifts are listed in ppm with the CDCl$_3$ carbon peak set to 77.23 ppm. For samples run in D$_2$O, DSS was used as the external standard. $^{19}$F chemical shifts are listed in ppm with CFCl$_3$ as the external standard for samples run in CDCl$_3$ and TFA as the external standard for samples run in D$_2$O. Mass spectra were obtained on a VG70-250SE mass spectrometer. Column chromatography was carried out with Merck silica gel 60 (230–400 mesh ASTM). TLC was run with EM Science from Aldrich Chemical Co. and were used without purification. All solvents were purchased from Fisher Scientific. Anhydrous THF was distilled from sodium metal under nitrogen.

Example 1

6-Oxo2-benzyl-2-azabicyclo[2.2.1]heptan-3-one (4). 6-exo-Acetoxy-2-benzyl-7-anti-bromo-2-azabicyclo[2.2.1] heptan-3-one (2.15 g, 6.6 mmol) was added to a solution of tributyltin hydride (2.9 g, 9.9 mmol) and AIBN (20 mg) in anhydrous benzene (20 mL). (Qiu, J.; Silverman, R. B. A New Class of Conformationally Rigid Analogues of 4-Amino-5-halopentanoic Acids, Potent Inactivators of γ-Aminobutyric Acid Aminotransferase. *J. Med. Chem.* 2000, 43, 706–720.) The resultant solution was heated at reflux and stirred for 12 h. After the solution was concentrated under reduced pressure, the residue was purified by flash column chromatography on silica gel, eluting with ethyl acetate/hexane (2:3), to afford 6-exo-acetoxy-2-benzyl-2-azabicyclo [2.2.1]heptan-3-one (1.37 g, 85%) as a colorless oil. $^1$HNMR (300 MHz, CDCl$_3$) 7.22 (5H, m, ArH), 4.76 (1H, m, H$_6$), 4.65 (1H, d, J, 15 Hz, ArCH$_2$), 4.0 (1H, d, 15 Hz, ArCH$_2$), 3.67 (1H, m, H$_1$), 2.80 (1H, m, H$_4$), 1.80–2.20 (4H, m, H$_5$ and H$_7$), 2.01 (3H, s, CH$_3$CO$_2$); m/z (EI) 260, 216, 173, 91, 65; HRMS (EI) calcd for C$_{15}$H$_{17}$NO$_3$ M 259.1208, found M 259.1210.

6-exo-Acetoxy-2-benzyl-2-azabicyclo[2.2.1]heptan-3-one (1.2 g, 4.6 mmol) was added to a stirred suspended solution of K$_2$CO$_3$ (1.9 g, 13.8 mmol) in methanol (15 mL) and water (5 mL). After being stirred for 3 h, the reaction mixture was concentrated under reduced pressure. The resultant aqueous layer was extracted with ethyl acetate (3×30 mL). The organic layer was washed with brine (25 mL) and dried over anhydrous $Na_2SO_4$. The solvent was concentrated under reduced pressure to afford 6-exo-hydroxy-2-benzyl-2-azabicyclo[2.2.1]heptan-3-one (0.99 g, 99%) as a solid. $^1$HNMR (300 MHz, $CDCl_3$) 7.20 (5H, m, ArH), 4.60 (1H, d, J, 15 Hz, $ArCH_2$), 4.04 (1H, d, 15 Hz, $ArCH_2$), 4.00 (1H, m, $H_6$), 3.54 (1H, m, $H_1$), 2.77 (1H, m, $H_4$), 1.5–2.2 (4H, m, $H_5$ and $H_7$); m/z (EI) 217, 173, 144, 91, 65; HRMS (EI) calcd for $C_{13}H_{15}NO_2$ M 217.1103, found M 217.1104.

4-Methylmorpholine N-oxide (0.77 g, 6.6 mmol), tetrapropylammonium perruthenate (TPAP) (5 mg) and 4 Å sieves were added to a stirred solution of 6-exo-hydroxy-2-benzyl-2-azabicyclo[2.2.1]heptan-3-one (0.67 g, 3.3 mmol) in anhydrous $CH_2Cl_2$ (10 mL). After being stirred for 14 h, the mixture was concentrated under reduced pressure. The resultant slurry was loaded on the flash silica gel column directly, eluting with EtOAc/hexane (2:3), to afford 4 (0.5 g, 75%) as a colorless solid. $^1$HNMR (300 MHz, $CDCl_3$) 7.30 (5H, m, ArH), 4.80 (1H, d, J, 15.1 Hz, $ArCH_2$), 3.95 (1H, d, 15 Hz, $ArCH_2$), 3.60 (1H, m, $H_1$), 3.07 (1H, m, $H_4$), 2.33–2.20 (3H, m, $H_5$ and $H_7$), 1.90 (1H, d, 10 Hz, $H_5$); m/z (EI) 215, 187, 132, 91, 65; HRMS (EI) calcd for $C_{13}H_{13}NO_2$ M 215.0946, found M 215.0949.

Example 2

6-exo-Trimethylsilylmethyl-6-endo-hydroxyl-2-benzyl-2-azabicyclo [2.2.1]heptan-3-one (5). (Trimethylsilylmethyl)magnesium chloride (1M, 3.7 mL, 3.7 mmol) was injected to a stirred solution of 6-oxo-2-benzyl-2-azabicyclo[2.2.1]heptan-3-one (4) (0.50 g, 2.5 mmol) in anhydrous THF (10 mL) at −30° C. under $N_2$ protection. After being stirred for 5 h at −30° C., the reaction mixture was stirred overnight at room temperature. The reaction mixture was treated with saturated $NH_4Cl$ (20 mL). The resultant aqueous layer was extracted with ethyl acetate (3×25 mL). The combined organic layers were washed with water (20 mL), brine (25 mL), dried over anhydrous $Na_2SO_4$, and concentrated under reduced pressure. The residue was purified by flash column chromatography on silica gel, eluting with ethyl acetate/hexane (1:3), to afford 5 (0.23 g, 38%) as a colorless solid. $^1$HNMR (300 MHz, $CDCl_3$) 7.33 (5H, m, ArH), 5.14 (1H, d, J, 15.1 Hz, $ArCH_2$), 4.07 (1H, d, J 15 Hz, $ArCH_2$), 3.33 (1H, d, t, J 1.6 Hz, $H_1$), 2.77 (1H, dd, J 3.6, 1.6 Hz, $H_4$), 2.03–1.67 (4H, $H_5$ and $H_7$), 1.12 (1H, d, J 3.3 Hz, $CH_2Si$), 0.11 (9H, m, $Si(CH_3)_3$); $^{13}$CNMR (300 MHz, $CDCl_3$) 177.1, 137.8, 128.9, 128.3, 127.6, 83.1, 68.7, 47.3, 46.0, 43.4, 41.0, 31.1, 0.64; m/z (EI) 303, 189, 173, 145, 91, 73; HRMS (EI) calcd for $C_{17}H_{25}NO_2Si$ M 303.1655, found M 303.1657.

Example 3

6-Methylenyl-2-benzyl-2-azabicyclo[2.2.1]heptan-3-one (6). 4-Dimethylaminopyridine (1.71 g, 14 mmol) and trifluoroacetic anhydride (1.47 g, 7.0 mmol) were added to a stirred solution 5 (0.21 g, 0.7 mmol) in anhydrous THF (10 mL) at room temperature. After the reaction mixture was stirred for 3 h, tetrabutylammonium bromide (3.38 g, 10.5 mmol) and potassium fluoride (1.22 g, 21 mmol) were added to the reaction mixture. The resultant mixture was stirred for 15 h at 50° C. The reaction mixture was diluted with saturated $NH_4Cl$ (25 mL) and the aqueous layer was extracted with ethyl acetate (3×40 mL). The combined organic layers were washed with water (25 mL) and brine (25 mL), and dried over anhydrous $Na_2SO_4$, and concentrated under reduced pressure. The residue was purified by flash column chromatography on silica gel, eluting with ethyl acetate/hexane (1:3), to afford 6 (0.13 g, 86%) as a colorless solid. $^1$HNMR (300 MHz, $CDCl_3$) 7.33 (5H, m, ArH), 5.05 (1H, s, $C=CH_2$), 4.95 (1H, s, $C=CH_2$), 4.79 (1H, d, J, 15.3 Hz, $ArCH_2$), 3.75 (1H, s, $H_1$), 3.72 (1H, d, J 15.3 Hz, $ArCH_2$), 2.92 (1H, dd, J 1.2, 2.7 Hz, $H_4$), 2.44 (1H, m, $H_{5exo}$ or $H_{5endo}$), 2.24 (1H, m, $H_{5exo}$ or $H_{5endo}$), 2.00 (1H, m, $H_{7anti}$ or $H_{7syn}$), 1.56 (1H, m, $H_{7anti}$ or $H_{7syn}$), $^{13}$C NMR (300 MHz, $CDCl_3$) 196.1, 178.6, 146.2, 137.4, 128.8, 128.3, 127.6, 107.4, 64.4, 54.7, 44.3, 40.4, 31.9; m/z (EI) 213, 172, 106, 91; HRMS (EI) calcd for $C_{15}H_{15}NO$ M 213.1154, found M 213.1162.

Example 4

3β-Amino-4-methylenylcyclopentane-1β-carboxylic acid (7). Freshly-cut pieces of sodium (0.16 g) were added to a stirred solution of liquid $NH_3$ (8 mL) and t-BuOH (2 mL) at −78° C. to afford a deep blue solution. Then, a solution 6 (0.11 g, 0.51 mmol) in THF (8 mL) was stepwise added to the stirred sodium-liquid ammonium solution at −78° C. After the resulting solution was stirred for 10 min at 78° C., the solution was raised to −30 ° C. and stirred for 4 min. Then, the solution was cooled back to −78° C. Acetic acid (2 mL) was added slowly. After the solution was allowed to warm to room temperature, the resultant slurry was filtered and washed with ethyl acetate (100 mL). The organic solution was concentrated under reduced pressure to afford a solid residue. Without any purification, the residue was added to a stirred solution of acetic acid (5 m) and 4N HCl (5 mL). The resulting solution was stirred at 70° C. for 5 h, and concentrated in vacuo to give a solid. The solid was purified by ion-exchange chromatography (AG® 50W-X8), eluting with water and 0.5 M $NH_4OH$, to afford 7 (0.065 g, 90%) as a colorless solid. $^1$HNMR (300 MHz, $D_2O$) 5.15 (1H, m, $C=CH_2$), 5.07 (1H, m, $C=CH_2$), 3.97 (1H, m, $H_3$), 2.61 (1H, m, $H_1$), 2.68–2.39 (2H, m, $H_2$), 2.20 (1H, ddd, J 14.2, 7.2, 7.0 Hz, $H_{5\alpha}$ or $H_{5\beta}$), 1.73 20 (1H, ddd, J 14.2, 7.2, 7.0 Hz, $H_{5\alpha}$ or $H_{5\beta}$); m/z (EI) 141, 96, 69; HRMS (EI) calcd for $C_7H_{11}O_2N$ M 141.0790, found M 141.0787, CHN analysis calcd for $C_7H_{11}O_2N$, H% 7.85 C% 59.56 N% 9.92, found H% 7.88 C% 59.23 N% 9.62.

Example 5

(1S, 4S)-6-Difluoromethylenyl-2-(4'-methoxybenzyl)-2-azabicyclo[2.2.1]heptan-3-one (13). At −78° C., $^t$BuLi (1.7 M in pentane, 1.73 mL, 2.94 mmol) was slowly added to a stirred solution of diethyl (difluoromethyl)phosphonate (0.48 mL, 2.94 mmol) in anhydrous THF (15 mL). After being stirred for 0.5 h at −78° C., 12 (0.60 g, 2.45 mmol) in anhydrous THF (20 mL) was slowly added via syringe. Stirring continued for 1 h at −78° C., then the solution was allowed to warm to room temperature and heated to reflux for 24 h. Compound 12 is known and available in the, art, and can be prepared as described in Qiu, J.; Silverman, R. B. A New Class of. Conformationally Rigid Analogues of 4-Amino-5-halopentanoic Acids, Potent Inactivators of γ-Aminobutyric Acid Aminotransferase. *J. Med. Chem.* 2000, 43, 706–720. After the reaction had cooled down, THF was evaporated, and saturated $NH_4Cl$ solution (20 mL) was added to the residue, which was extracted with EtOAc (3×20 mL). The organic layer was washed with brine (2×20 mL), dried4over anhydrous $Na_2SO_4$, and concentrated under reduced pressure. The residue was purified by flash column chromatography, eluting with hexanes/ethyl acetate (2:1) to give 13 (0.47 g, 68%) as a colorless oil: $^1$H NMR (400 MHz, CDCl$_3$) δ 7.18 (d, J 8.4 Hz, 2H), 6.07 (d, J 8.4 Hz, 2H), 4.63 (d, J 14.8 Hz, 1H), 4.14 (s. 1H), 3.80 (s, 3H), 3.78 (d, J 14.8 Hz, 1H), 3.00 (s, 1H), 2.50 (dt, J 15.2, 3.6 Hz, 1H), 2.27 (dd, J 15.2, 2.4 Hz, 1H), 2.00 (d, J 9.2 Hz, 1H) 1.53 (d, 9.6 Hz, 1H); $^{13}$C NMR (100 MHz, CDCl$_3$) δ 177.37, 159.13, 152.19 (dd, J 285.7, 281.2 Hz), 129.59, 128.47, 114.13, 88.95 (dd, J 25.6, 22.2 Hz), 58.38 (d, J 5.3 Hz), 55.50, 45.60, 44.59, 40.96, 27.43; $^{19}$F NMR (376 MHz, CDCl$_3$) δ 42.64 and 41.01 (2 dd, J 60.2, 2.3 Hz, 2F). HRMS (EI) C$_{15}$H$_{15}$NO$_2$F$_2$ calcd M 279.1071, found M 279.10701.

Example 6

(1S, 4S)-6-Difluoromethylenyl-2-azabicyclo[2.2.1]heptan-3-one (14). Compound 13 (86.9 mg, 0.31 mmol) was dissolved in CH$_3$CN (1.75 mL). A solution of ceric ammonium nitrate (512 mg, 0.93 mmol) in water (0.87 mL) was slowly added. The resulting solution was stirred at room temperature for 4 h. The reaction mixture was then diluted with ethyl acetate (20 mL), washed with brine (2×10 mL), and dried over anhydrous Na$_2$SO$_4$. After being concentrated under reduced pressure, the residue was purified by flash column chromatography, eluting with hexanes/ethyl acetate (1:1) to give the desired product as a colorless oil (33.6 mg, 68%). $^1$H NMR (400 MHz, CDCl$_3$) δ 5.48 (br s, 1H), 4.40 (s, 1H), 2.93 (s, 1H), 2.54 (dd, J 15.2, 2.8 Hz, 1H), 2.32 (d, J 15.2 Hz, 1H), 2.15 (d, J 9.6 Hz, 1H), 1.64 (d, J 10.0 Hz, 1H); $^{19}$F NMR (376 MHz, CDCl$_3$) δ 42.85 and 40.00 (2d, J 60.2 Hz, 2F); HRMS (EI) C$_7$H$_7$NOF$_2$ calcd M 159.0496, found M 159.04673.

Example 7

(1S, 3S)3-Amino-4-difluoromethylenyl-1-cyclopentanoic acid (15). To lactam 14 (20.0 mg, 0.13 mmol) was added 4 mL of 4 N HCl. The solution was stirred at 70° C. for 10 h. After being washed with ethyl acetate (3×4 mL), the water layer was evaporated under reduced pressure to give a yellow solid. Recrystallization with ethanol/ether gave a white solid, which was then loaded on a cation-exchange column (AG50W-X8) and eluted with 0.2 N ammonium hydroxide to give the free amino acid 15 as a white solid (16 mg, 72%). $^1$H NMR (400 MHz, D$_2$O) δ 4.44 (s, 1H), 2.92 (m, 1H), 2.74 (m, 1H), 2.57 (dd, J 16.4, 3.6 Hz, 1H), 2.34 (m 1H), 2.02 (d, J 14.8 Hz, 1H); $^{13}$C NMR (126 MHz, D$_2$O) δ 186.08, 155.30 (t, J 288.7 Hz), 92.19 (m), 53.16 (d, J 3.8 Hz), 48.01, 37.89, 32.45; $^{19}$F NMR (376 MHz, D$_2$O) δ −8.43 and −9.02 (2d, J 46.3 Hz, 2F); MS (ESI) C$_7$H$_9$NO$_2$F$_2$ calcd M+H 178, found M+H 178.

Example 8

(E/Z)-(1S,4S)-6-(1'-Fluoro-1'-phenylsulfonyl)methylenyl-2-(4'-methoxybenzyl)2-azabicyclo [2.2.2]heptan-3-one (16). To anhydrous THF (3 mL) was added fluoromethyl phenylsulfone (130 mg, 0.75 mmol) and diethyl chlorophosphate (0.11 mL, 0.74 mmol). After cooling to −78° C. under nitrogen, lithium bis(trimethylsilyl)amide (1.0 M in THF, 1.65 mL, 1.65 mmol) was slowly added. After stirring for 1 h, a solution of 12 (91.3 mg, 0.37 mmol) in anhydrous THF (3 mL) was slowly added via cannula. The solution was then warmed to room temperature and stirred overnight. After being quenched with saturated NH$_4$Cl solution (10 mL), THF was evaporated and the resulting solution was extracted with ethyl acetate (3×10 mL). The organic layer was combined, washed with brine, and dried over anhydrous Na$_2$SO$_4$. This solution was then concentrated under reduced pressure and purified with flash column chromatography, eluting with hexanes/ethyl acetate (1:0 to 1:2), giving an inseparable cis/trans mixture (16) (4.4:1 as seen from NMR, 119 mg, 80%) as a colorless oil. $^1$H NMR for the major product (400 MHz, CDCl$_3$) δ 7.94 (d, J 8.0 Hz, 2H), 7,72 (t, J 7.4 Hz, 1H), 7.61 (t, J 7.6 Hz, 2H), 7.33 (d, J 8.4 Hz, 2H), 6.90(d, J 8.8 Hz, 2H), 5.24 (s, 1H), 4.77(d, J 14.8 Hz, 1H), 3.82 (s, 3H), 3.79 (d, J 14.8 Hz, 1H), 3.00 (s, 1H), 2.49–2.66 (m, 2H), 2.10 (d, J 9.2 Hz 1H), 1.63 (d, J 8.8 Hz, 1H).

Example 9

(E)-(1S,4S)-6-Fluoromethylenyl-2-(4'-methoxybenzyl)2-azabicyclo[2.2.2]heptan-3-one (17) and (Z)-(1S,4S)-fluoromethylenyl-2-(4'-methoxybenzyl)-2-azabicyclo[2.2.2]heptan-3-one (18). Compound 16 (100 mg, 0.25 mmol) was dissolved in anhydrous methanol (10 mL) under nitrogen and put in an ice-salt bath. Magnesium turnings (0.30 g,. 12.5 mmol) and mercury (II) chloride (60 mg, 0.22 mmol) were added. The solution was stirred for 2 h, then warmed to room temperature and stirred overnight. The reaction mixture was poured into 1 N HCl (10 mL). Methanol was evaporated under reduced pressure and the resulting water solution was extracted with ethyl acetate (3×10 mL). The organic layer was combined, washed with saturated NaHCO$_3$ solution (2×10 mL), brine (2×10 mL), and dried over anhydrous Na$_2$SO$_4$. After concentration under reduced pressure, the residue was purified, by column chromatography with hexanes/ethyl acetate (3:1), giving compound 17 (33.8 mg, 52%) and 18 (12.9 mg, 20%), both as colorless oils.

For 17: $^1$H NMR (500 MHz, CDCl$_3$) δ 7.15 (d, J 8.5 Hz, 2H), 6.87 (d, J 8.5 Hz, 2H), 6.65 (d, J 82.9 Hz, 1H), 4.66 (d, J 15.0 Hz, 1H), 3.83 (s, 1H), 3.81 (s, 3H), 3.72 (d, J 15.0 Hz, 1H), 2.98 (s, 1H), 2.55 (dd, J 16.0, 2.5 Hz, 1H), 2.36 (dd, J 16.0, 1.5 Hz, 1H), 2.02 (d, J 8.0 Hz, 1H), 1.53 (d, J 9.5 Hz, 1H).

For 18: $^1$H NMR (500 MHz, CDCl$_3$) δ 7.21 (d, J 8.5 Hz, 2H), 6.87 (d, J 8.5 Hz, 2H), 6.54 (d, J 84.9 Hz, 1H), 4.67 (d, J 15.0 Hz, 1H), 4.36 (s, 1H), 3.81 (s, 3H), 3.67 (d, J 15.0 Hz, 1H), 2.96 (s, 1H), 2.43 (d, J 14.0 Hz, 1H), 2.21 (d, J 15.0 Hz, 1H), 1.97 (d, J 9.5 Hz, 1H), 1.48 (d, J 9.5 Hz, 1H).

Example 10

(E)-(1S,4S)-6-Fluoromethylenyl-2-azabicyclo[2.2.2]heptan-3-one (19). In an Eppendorf tube, 17 (10.2 mg, 39 μmol) was dissolved in acetonitrile (0.22 mL). To this solution was added a solution of ceric ammonium nitrate (64mg, 117 μmol) in water (60 μL). After being stirred at room temperature for 3 h, the reaction mixture was diluted with ethyl acetate (10 mL), washed with brine (2×5 mL), and dried over anhydrous Na$_2$SO$_4$. After concentration under reduced pressure, the residue was purified by column chromatography, eluting with hexanes/ethyl acetate (1:1) to give 19 as a colorless oil (2.0 mg, 36%). $^1$H NMR(400 MHz, CDCl$_3$) δ 6.83 (d, J 83.2 Hz, 1H), 5.48 (br s, 1H), 4.15 (s, 1H), 2.90 (s, 1H), 2.60 (d, J 16.8 Hz, 1H), 2.39 (d, J 15.6Hz, 1H), 2.15 (d, J 9.2 Hz, 1H), 1.61 (d, J 9.2 Hz, 1H); $^{19}$F NMR (376 MHz, CDCl$_3$) δ −2.75 (d, J 83.6 Hz, 1F).

Example 11

(Z)-(1S, 4S)-6-Fluoromethylenyl-2-azabicyclo[2.2.2]heptan-3-one (21). $^1$H NMR (400 MHz, CDCl$_3$) δ 6.47 (d, J 85.6 Hz, 1H), 5.40 (s, 1H), 4.61 (s, 1H), 2.89 (s, 1H), 2.47 (d, J 14.8 Hz, 1H), 2.26 (d, J 16.0 Hz, 1H), 2.13 (d, J 9.2 Hz, 1H); $^{19}$F NMR (376 MHz, CDCl$_3$) δ −0.27 (d, J 84.0 Hz, 1F).

Example 12

(E)-(1S, 3S)-3-Amino-4-fluoromethylenyl-1-cyclopentanoic acid, hydrochloride salt (20). To compound 19 (2.0 mg, 14 μmol) was added 4 N HCl (4 mL). The solution was heated to 70° C. and stirred for 10 h. Then it was cooled, washed with ethyl acetate (2×4 mL), and evaporated under reduced pressure to give a white solid (2.0 mg, 72%). $^1$H NMR (400 MHz, D$_2$O) δ 6.93 (d, J 81.2 Hz, 1H), 4.33 (m, 1H), 3.06 (t, J 8.0 Hz, 1H), 2.91 (m, 1H), 2.71 (m, 1H), 2.48 (t, J 6.8 Hz, 1H), 2.03 (t, 6.8 Hz, 1H); $^{19}$F NMR (376 MHz, D$_2$O) δ −48.59 (d, J 78.7 Hz, 1F).

Example 13

(Z)-(1S, 3S)-3-Amino-4-fluoromethylenyl-1-cyclopentanoic acid, hydrochloride salt (22). $^1$H NMR (400 MHz, D$_2$O) δ 6.82 (d, J 82.4 Hz, 1H), 4.50 (s, 1H), 3.00 (p, J 8.0 Hz, 1H), 2.70 (m, 1H), 2.48–2.62 (m, 2H), 1.99 (m, 1H); $^{19}$F NMR (376 MHz, D$_2$O) δ −50.47 (d, J 82.5 Hz, 1F).

Example 14a

Time dependent Inactivation of GABA-AT by 15 and (S)-vigabatrin. Incubation solutions (100 μL) contain commercially available GABA-AT (20 μL, 1.84 mg/mL, specific activity 2.5 unit/mg), potassium pyrophosphate buffer (60 μL, 50 mM, pH 6.5), α-ketoglutarate (10 μL, 16 mM in 50 mM potassium pyrophosphate buffer, pH 6.5), 2-mercaptoethanol (2 mM), and 15 or (S)-vigabatrin (10 μL, with varied concentrations of compounds in 50 mM potassium pyrophosphate buffer, pH 6.5). The concentrations for 15 and vigabatrin are as follows: 66.8, 74.1, 95.5, 111.2 μM for 15 and 334, 417.5, 477.0, 556.4, 668 μM for (S)-vigabatrin. At timed intervals (about one minute for 15 and three minutes for (S)-vigabatrin), aliquots (20 μL from the incubation solution were added to the assay solution (575 μL, 50 mM potassium pyrophosphate buffer containing 5.3 mM of α-ketoglutarate, 11 mM of GABA, 1.1 mM of NADP$^+$and 4.8 mM of 2-mercaptoethanol) with excess SSDH. Rates were measured spectrophotometrically at 340 nm, and the logarithm of the remaining activity (percentage) was plotted against time for each concentration to determine the half-life. Then a secondary plot of half-life versus the reciprocal of inactivator concentration was obtained to determine $K_I$ and $k_{inact}$.

Example 14b

At pH 8.5 and 25° C. the specificity constant ($k_{inact}/K_I$) for the difluoromethylene inactivator is 186 times that for vigabatrin (see Table 1 below).

TABLE 1

| Difluoromethylene Inactivator | Vigabatrin |
|---|---|
| $K_I$ = 9.7 μM | $K_I$ = 850 μM |
| $k_{inact}$ = 0.50 min$^{-1}$ | $k_{inact}$ = 0.24 min$^{-1}$ |
| $k_{inact}/K_I$ = 0.052 μMmin$^{-1}$ | $k_{inact}/K_I$ = 0.00028 μMmin$^{-1}$ |

Example 14c

Using experimental protocols such as those provided in example 14a, compounds 20 and 22 are used effectively to inhibit GABA-AT. Comparable results are obtained with the trans isomer.

Example 15

Studies were undertaken to characterize the addition product of GABA-AT and an inhibitor compound of this invention. To that effect, utilizing procedures analogous to that described in example 14a, two incubation solutions were prepared, one with 543 equiv. of a difluoro-substituted compound and another with 1 equiv. of the same compound. Each was monitored for fluoride ion using an Orion 720A pH meter and an Orion 96-09 fluoride/combination fluoride electrode. (A standard curve was made each time before measuring fluoride concentration.)

In the presence of 543 equiv. of the difluoro compound, the fluoride ion concentration was 1.07 equiv. after inactivation, 4.4 equiv. after 24 hours, and 4.9 equiv. after 48 hours. With 1 equiv. of the subject difluoro inactivator compound, fluoride ion concentration was 0.75 equiv. at 15% enzyme activity (about 1 hour, 33 minutes) and 1.55 equiv. at 24 hours.

The data of this example show that one equiv. of fluoride ion is released from the subject inactivator compound after complete loss of enzymatic activity, but that one or more additional fluoride ions are lost non-enzymatically thereafter, slowly over time, possibly from a metabolite of the addition product complex.

We claim:

1. A γ-aminobutyric acid aminotransferase inhibitor compound selected from compounds of a formula

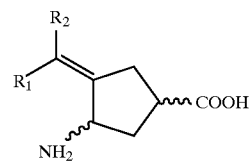

wherein $R_1$ and $R_2$ are selected from H and F, and at least one of $R_1$ and $R_2$ is F; and salts thereof.

2. The inhibitor compound of claim 1 wherein $R_1$ and $R_2$ are F.

3. The inhibitor compound of claim 2 wherein said NH$_2$ and COOH substituents have a stereochemical relationship selected from cis and trans.

4. The inhibitor compound of claim 3 wherein said substituents are cis.

5. The inhibitor compound of claim 2 selected from an ammonium salt and a carboxylate salt of said compound.

6. The inhibitor compound of claim 5 wherein said compound is an ammonium salt, and the counter ion is the conjugate base of a protic acid.

7. The inhibitor compound of claim 5 wherein said compound is a carboxylate, and the counter ion is selected from the conjugate acid of an amine, alkaline and alkaline-earth base.

8. The inhibitor compound of claim 5 wherein said compound is selected from an ammonium hydrochloride salt and a sodium carboxylate.

9. The inhibitor compound of claim 1 wherein one of said $R_1$ and $R_2$ is F.

10. The inhibitor compound of claim 9 wherein $R_1$ is F, and said F and COOH substituents have a Z configuration.

11. The inhibitor compound of claim 10 wherein said NH$_2$ and COOH substituents have a stereochemical relationship selected from cis and trans.

12. The inhibitor compound of claim 9 wherein $R_1$ is F, and said F and COOH substituents have an E configuration.

13. The inhibitor compound of claim 12 wherein said NH$_2$ and said COOH substituents have a stereochemical relationship selected from cis and trans.

14. The inhibitor compound of claim 9 selected from an ammonium salt and a carboxylate salt of said compound.

15. An enzyme-inactivator complex comprising the addition product of a γ-aminobutyric acid aminotransferase and a compound selected from compounds of a formula

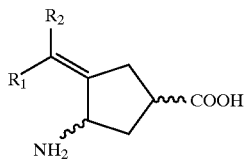

wherein $R_1$ and $R_2$ are selected from H and F, and at least one of $R_1$ and $R_2$ is F; and salts thereof.

16. The enzyme-inactivator complex of claim 15 wherein $R_1$ and $R_2$ of said compound are F.

17. The enzyme-inactivator complex of claim 16 wherein said $NH_2$ and COOH substituents have a stereochemical relationship selected from cis and trans.

18. The enzyme-inactivator complex of claim 15 wherein one of said $R_1$ and $R_2$ is F.

19. The enzyme-inactivator complex of claim 15 wherein said compound is selected from an ammonium salt and a carboxylate salt of said compound.

20. The enzyme-inactivator complex of the claim 15 wherein said addition product further comprises a pyridoxal-5'-phosphate cofactor.

21. A method of inhibiting a γ-aminobutyric acid aminotransferase comprising contacting a γ-aminobutyric acid aminotransferase with an effective amount of a compound selected from compounds of a formula

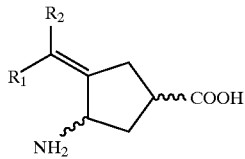

wherein $R_1$ and $R_2$ are selected from H and F and at least one of $R_1$ and $R_2$ is F; and salts thereof.

22. The method of claim 21 wherein $R_1$ and $R_2$ are F.

23. The method of claim 22 wherein said $NH_2$ and COOH substituents have a stereochemical relationship selected from cis and trans.

24. The method of claim 21 wherein one of said $R_1$ and $R_2$ is F.

25. The method of claim 21 wherein said aminotransferase comprises a pyridoxal-5'-phosphate cofactor.

26. The method of claim 21 wherein said compound is selected from an ammonium salt and a carboxylate salt of said compound.

27. A method of using an electron-deficient exocyclic methylene moiety to inhibit γ-aminobutyric acid aminotransferase activity, said method comprising: providing a compound selected from compounds of a formula

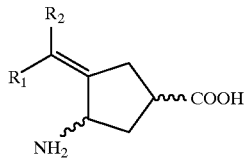

wherein $R_1$ and $R_2$ are selected from H and F, and at least one of $R_1$ and $R_2$ is F; and salts thereof; and contacting a γ-aminobutyric aminotransferase with said compound, said exocyclic methylene moiety of said compound capable of binding to an active site of said aminotransferase.

28. The method of claim 27 wherein $R_1$ and $R_2$ are F.

29. The method of claim 28 wherein said $NH_2$ said COOH substituents have a stereochemical relationship selected from cis and trans.

30. The method of claim 27 wherein one of said $R_1$ and $R_2$ is F.

31. The method of claim 27 wherein said aminotransferase comprises a pyridoxal-5'-phosphate cofactor.

32. The method of claim 27 wherein said compound is selected from an ammonium salt and a carboxylate salt of said compound.

33. The compound of claim 1 which is (1S,3S)-3-amino-4-difluoromethylenyl-1-cyclopentanoic acid.

34. The compound of claim 12 which is E-(1S,3S)-3-amino-4-fluoromethylenyl-1-cyclopentanoic acid.

35. The compound of claim 10 which is Z-(1S,3S)-3-amino-4-fluoromethylenyl-1-cyclopentanoic acid.

* * * * *

UNITED STATES PATENT AND TRADEMARK OFFICE
CERTIFICATE OF CORRECTION

PATENT NO. : 6,794,413 B1  
APPLICATION NO. : 10/623152  
DATED : September 21, 2004  
INVENTOR(S) : Richard B. Silverman et al.

It is certified that error appears in the above-identified patent and that said Letters Patent is hereby corrected as shown below:

Col. 1, Line 22: "glutaric " should be --glutamic--

Col. 1, Line 27: "glutamnic" should be --glutamic--

Col. 7, Line 51: "fill" should be --full--

Signed and Sealed this

Twenty-eighth Day of November, 2006

JON W. DUDAS  
*Director of the United States Patent and Trademark Office*